United States Patent
Khoury et al.

(10) Patent No.: US 10,512,477 B2
(45) Date of Patent: Dec. 24, 2019

(54) DEVICES FOR MANIPULATING TISSUE AND RELATED METHODS

(71) Applicant: Boston Scientific Scimed, Inc., Maple Grove, MN (US)

(72) Inventors: Elias Khoury, Maple Grove, MN (US); Wade Strelow, Jr., Maple Grove, MN (US); Steven Larsen, Lino Lakes, MN (US); Ismail Guler, Maple Grove, MN (US); Brian Hanson, Shoreview, MN (US); Daniel Vancamp, Elk River, MN (US); Paul Smith, Smithfield, RI (US); Kevin McElwee, Franklin, MA (US); Oscar Carrillo, Jr., Attleboro, MA (US); Andrew Schaubhut, Stow, MA (US); Samuel Raybin, Marlborough, MA (US); Man Nguyen, Harvard, MA (US); Naroun Suon, Lawrence, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 524 days.

(21) Appl. No.: 15/218,153

(22) Filed: Jul. 25, 2016

(65) Prior Publication Data

US 2017/0027582 A1    Feb. 2, 2017

Related U.S. Application Data

(60) Provisional application No. 62/197,337, filed on Jul. 27, 2015.

(51) Int. Cl.
*A61B 17/221* (2006.01)
*A61B 17/3205* (2006.01)
(Continued)

(52) U.S. Cl.
CPC ...... *A61B 17/221* (2013.01); *A61B 17/32056* (2013.01); *A61B 17/12013* (2013.01);
(Continued)

(58) Field of Classification Search
CPC .................. A61B 17/221; A61B 17/32056
See application file for complete search history.

(56) References Cited

U.S. PATENT DOCUMENTS

| 5,417,684 A | 5/1995 | Jackson et al. |
| 6,773,432 B1 | 8/2004 | Clayman et al. |

(Continued)

OTHER PUBLICATIONS

International Search Report and Written Opinion issued in PCT/US2016/043967, dated Oct. 4, 2016 (14 pages).

*Primary Examiner* — Sarah W Aleman
(74) *Attorney, Agent, or Firm* — Bookoff McAndrews, PLLC

(57) ABSTRACT

A medical device may include an insertion device having a proximal end, a distal end, and a lumen extending therethrough. A snare device may be configured to transition between a retracted state within the lumen of the insertion device, and an extended state extending distally of the insertion device. The snare device may comprise a wire. A member may be disposed within the lumen of the insertion device. The member may be configured to maintain legs of the snare device in an open snare loop configuration in the extended state. In the open snare loop configuration, the wire may include an arcuate loop.

20 Claims, 6 Drawing Sheets

(51) Int. Cl.
  *A61B 17/12* (2006.01)
  *A61B 34/00* (2016.01)
  *A61B 17/00* (2006.01)
  *A61B 90/00* (2016.01)

(52) U.S. Cl.
  CPC ..... *A61B 34/73* (2016.02); *A61B 2017/00269* (2013.01); *A61B 2017/00358* (2013.01); *A61B 2017/00876* (2013.01); *A61B 2090/035* (2016.02)

(56) References Cited

U.S. PATENT DOCUMENTS

| | | |
|---|---|---|
| 2007/0250070 A1 | 10/2007 | Nobis et al. |
| 2009/0043154 A1 | 2/2009 | Okada |
| 2012/0283723 A1 | 11/2012 | Jenkins et al. |
| 2014/0228872 A1 | 8/2014 | Polo |
| 2014/0276911 A1 | 9/2014 | Smith et al. |
| 2015/0100062 A1 | 4/2015 | Smith et al. |

DEVICES FOR MANIPULATING TISSUE AND RELATED METHODS

CROSS-REFERENCE TO RELATED APPLICATIONS

This application claims the benefits of priority from U.S. Provisional Application No. 62/197,337, filed on Jul. 27, 2015, the entirety of which is incorporated herein by reference.

TECHNICAL FIELD

Aspects of the present disclosure generally relate to medical devices and procedures. In particular, aspects of the present disclosure relate to medical devices for manipulating, for example, resecting, grasping, and/or collecting tissue from a portion of a patient's body, such as, for example, snare devices.

BACKGROUND

Medical devices, such as endoscopes or other suitable introduction devices, are employed for a variety of diagnostic and surgical procedures, such as laparoscopy, arthroscopy, gynoscopy, thoracoscopy, and cystoscopy, etc. Many of these procedures are carried out for purposes of tissue resection, which generally includes removal of tissue of an organ or a gland to treat tumors, infestations, and the like. In particular, such procedures may be carried out by inserting an introduction device into a patient's body through a surgical incision, or via a natural anatomical orifice (e.g., mouth, vagina, or rectum), and performing the procedure or operation.

Snare devices, in particular, have been used in many medical procedures, including Endoscopic Mucosal Resection (EMR) and Endoscopic Sub-mucosal Resection (ESR), Polypectomy, Mucosectomy, etc., for resecting tissue from a target site. A snare device generally includes a snare loop formed by snare wires, which engages the tissue intended to be resected. The snare loop is controlled and operated at a proximal end of the device through a suitable actuating mechanism. However, in many conventional snare devices, the snare loop has a tendency to twist about itself, away from a plane of a layer of tissue, which may reduce the snare's ability to ensnare the desired tissue.

SUMMARY

Examples of the present disclosure relate to, among other things, medical devices such as snares, and related methods of use thereof. Each of the examples disclosed herein may include one or more of the features described in connection with any of the other disclosed examples.

In one example, a medical device may include an insertion device having a proximal end, a distal end, and a lumen extending therethrough. A snare device may be configured to transition between a retracted state within the lumen of the insertion device, and an extended state extending distally of the insertion device. The snare device may comprise a wire. A member may be disposed within the lumen of the insertion device. The member may be configured to maintain legs of the snare device in an open snare loop configuration in the extended state. In the open snare loop configuration, the wire may include an arcuate loop.

Aspects of the medical device may additionally and/or alternatively include one or more other features. The member may include a space occupier fixedly coupled to the insertion device. The space occupier may have a rounded rectangular cross-sectional shape. The space occupier may include a tapered proximal end. The space occupier may have an hourglass cross-sectional shape. The space occupier may define at least two channels along an exterior surface of the space occupier configured to receive the legs therein. The space occupier may be a polymer plug. The member may include at least one hollow insert fixedly coupled to the insertion device and configured to receive the legs therethrough. The insert may comprise a first portion having a first cross-sectional area and a second portion having a second cross-sectional area, wherein the first cross-sectional area is different from the second cross-sectional area. The second portion may be configured to receive the legs therethrough with a first degree of clearance while the first portion may be configured to receive the legs therethrough with a second degree of clearance. The first degree of clearance may be less than the second degree of clearance. The second portion may be flared outwardly relative to the first portion. The insert may include a rectangular channel having a width. Each leg may include a bend having a span, the span of each bend may be configured to be received within the channel when the leg is in a first state, and the span of each bend may be configured to obstruct receipt within the channel when the leg is in a second state. The span of each bend may be sized such that, when the bends are received within the channel of the insert, engagement between interior walls of the insert and the bend may be configured to maintain the arcuate loop in a single plane. The insert may include a pair of D-shaped channels configured to cooperate with the legs of the snare device and may maintain the arcuate loop in a single plane.

In another example, a medical device may include an insertion device having a proximal end, a distal end, and a lumen extending therethrough. A snare device may be configured to transition between a retracted state within the lumen of the insertion device, and an extended state extending distally of the insertion device. The snare device may include a wire defining legs. The medical device may further include magnetic material disposed along at least a portion of each leg. Additionally, the medical device may further include a magnet configured to cooperate with the magnetic material so as to maintain the legs in an open snare loop configuration. In the open snare loop configuration, the wire may comprise an arcuate loop.

Aspects of the medical device may additionally and/or alternatively include one or more other features. The magnet may include an annular magnet disposed on the distal end of the insertion device. Each leg may include a channel configured to receive magnetic material therein. Each leg may have a rectangular cross-sectional shape and each channel may have a rectangular cross-sectional shape. Each leg may have a circular cross-sectional shape and each channel has a rounded shape. The magnet may be an electromagnet and may be configured to be selectively activated and deactivated. The magnetic material may be neodymium based.

In another example, a method may comprise manipulating a snare device between a retracted stated within a lumen of an insertion device and an extended state extending distally of the insertion device. The snare device may include a wire defining legs and magnetic material disposed along at least a portion of each leg. The method may further include activating a magnet to attract the magnetic material. Further, the method may further include urging the legs toward an open snare loop configuration via the magnetic attraction between the magnet and the magnetic material.

Aspects of the method may additionally and/or alternatively include one or more other features. Each leg may comprise a channel configured to receive the magnetic material therein. The magnet may be an electromagnet and the magnetic material is neodymium based.

It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

DETAILED DESCRIPTION

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device. When used herein, "proximal" refers to a position relatively closer to the exterior of the body or closer to a user using the medical device. In contrast, "distal" refers to a position relatively further away from the user using the medical device, or closer to the interior of the body.

Figure 1A:
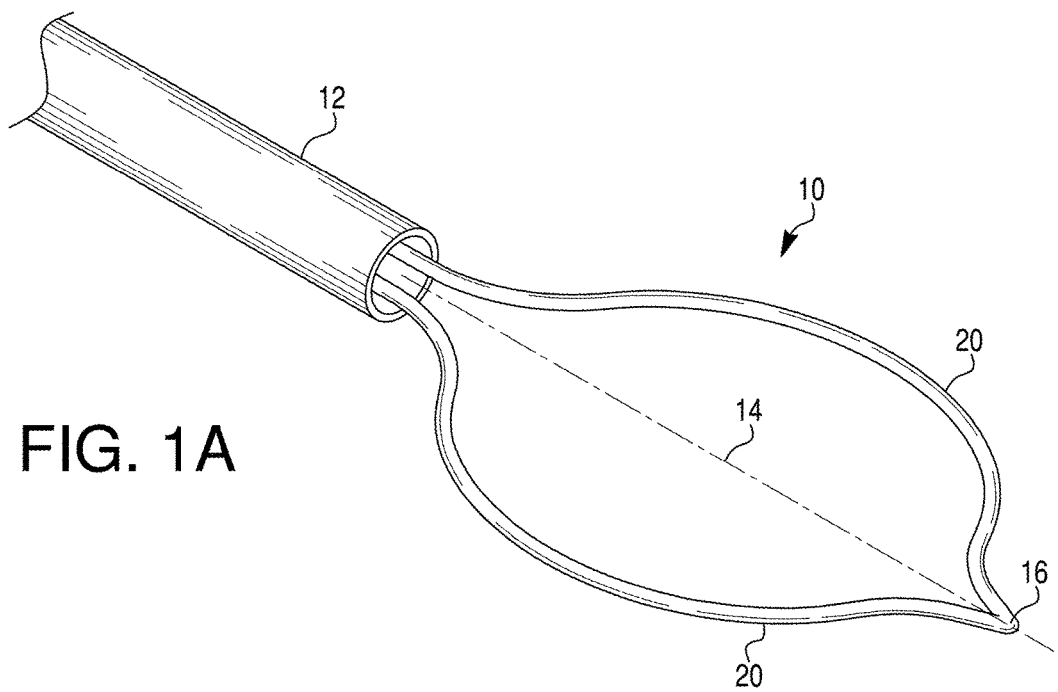
FIG. 1A depicts an exemplary snare device in an extended and expanded state.

The present disclosure is drawn to medical devices such as snare devices, and related methods of use thereof. FIG. 1A depicts a conventional snare device 10. Snare device 10 may be delivered to a target tissue via an insertion device 12. Insertion device 12 may include any device configured to deliver medical instruments, such as, snare device 10, into a subject's body. Insertion device 12 may be inserted into a variety of body openings, lumens, and/or cavities. For example, insertion device 12 may be inserted into any portion of a urinary tract, such as a ureter, a gastrointestinal lumen, such as an esophagus, a vascular lumen, and/or an airway. According to aspects of the present disclosure, insertion device 12 may be a ureteroscope, an endoscope, a hysteroscope, a uteroscope, a bronchoscope, a cystoscope, and similar devices. Alternatively, insertion device 12 may be a catheter or other sheath. Insertion device 12 may be single-use and disposable, or multiple-use and non-disposable. Insertion device 12 may have a circular cross-sectional shape, but other suitable cross-sectional shapes such as elliptical, oval, polygonal, or irregular may also be employed.

Once positioned within the subject's body, a user may move snare device 10 between an extended state (FIG. 1A) and a retracted state (not shown). In the extended state snare device 10 may extend distally out of the distal end of insertion device 12, and comprise an open snare loop configuration. In the open snare loop configuration, the wire may comprise an arcuate loop. The arcuate loop may be a flat or planar loop. Additionally, in the extended state, snare device 10 may be caused to expand to surround or otherwise engage, grasp, and/or collect tissue. In moving from the extended state to the retracted state snare device 10 may be drawn into the distal end of insertion device 12, and snare device 10 may be caused to contract to resect tissue.

For example, snare device 10 may be a single, continuous monofilament or multifilament piece of material, such as a wire, forming a loop and including legs 20. Legs 20 may extend proximally to a proximal portion (not shown) of medical device 10, where legs 20 may be associated with any appropriate user interface such as, for example, a handle (not shown). Alternatively, legs 20 may terminate proximally of a handle.

Figure 7:
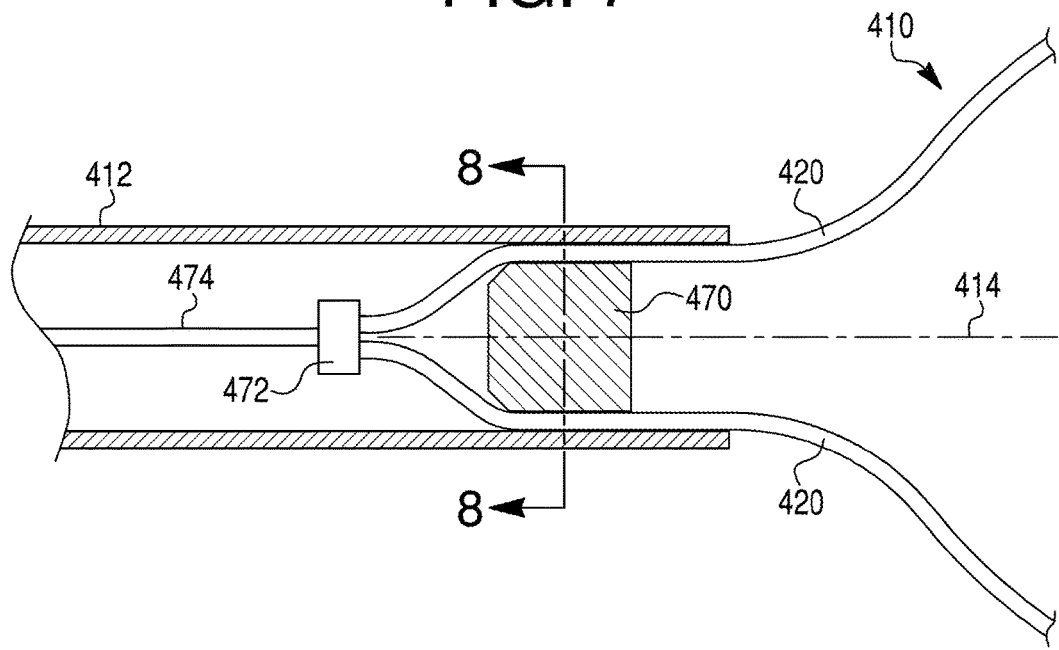
FIG. 7 depicts a cross-sectional view of an exemplary snare device, according to still further aspects of the present disclosure.

According to one aspect, proximal ends of legs 20 may be coupled to a handle (not shown) by an actuating member (see, e.g., actuating member 474 of FIG. 7), via a securement device, such as, for example, a hypotube or crimp (see, e.g., securement device 472 of FIG. 7). The handle may be configured to remain outside of the patient's body during a procedure and may allow a user to control snare device 10, for example, by applying an axially directed pushing or pulling force on one or both of the legs 20, to extend legs 20 out of the distal end of insertion device 12 or retract legs 20 into the distal end of insertion device 12, respectively.

Figure 1B:
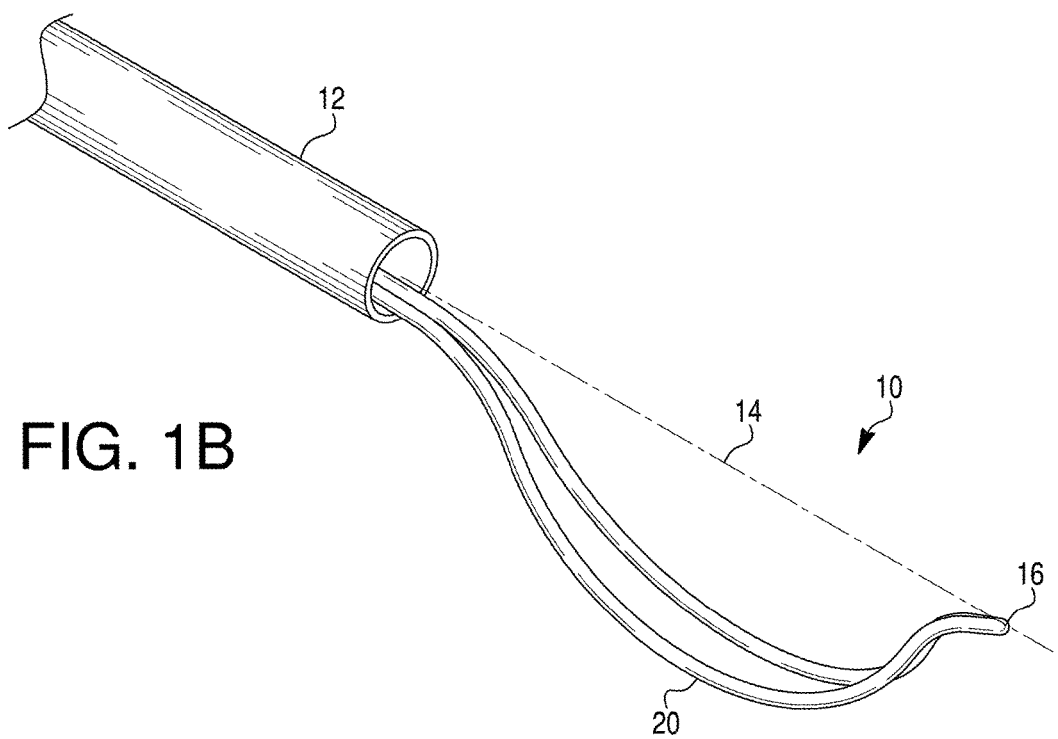
FIG. 1B depicts the exemplary snare device of FIG. 1A in an extended and folded state.

Snare device 10 may include any appropriate material, such as, for example, Nitinol. Snare device 10 may be heat set into an arcuate, circular, or otherwise curved shape as shown in FIG. 1A, and may include an atraumatic tip 16. In some instances, such a heat set construction may result in instability as there may be more than one natural position or configuration for snare device 10. For example, as shown in FIG. 1B, as snare device 10 contacts tissue to be resected, grasped, and/or collected, or as snare device 10 is drawn proximally towards insertion device 12, snare device 10 may twist, fold, and/or rotate about longitudinal axis 14 onto itself. That is, upon contact with tissue and or while being drawn into insertion device 12, the increased stress and/or strain imparted to snare device 10 may cause instability or torsion in snare device 10. This torsional instability in the heat set snare device 10 may cause snare device 10 to flip or otherwise deform into an unwanted configuration as shown in FIG. 1B.

Figure 2:
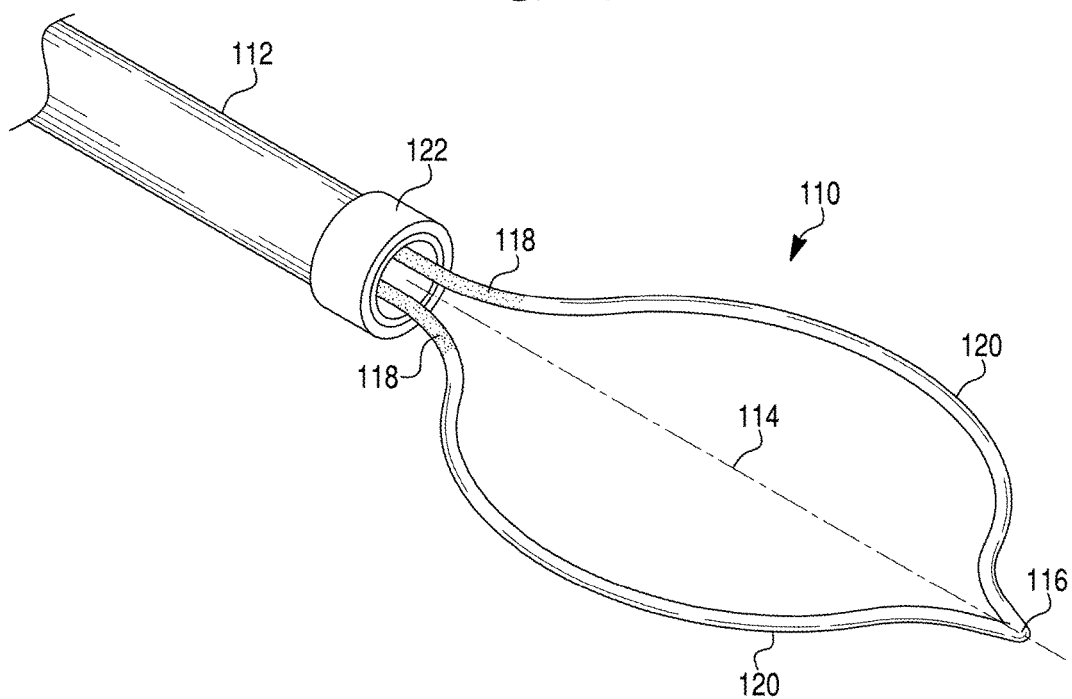
FIG. 2 depicts an exemplary snare device according to aspects of the present disclosure.

FIG. 2 depicts a snare device 110 extending along a longitudinal axis 114, according to an example of the present disclosure. Snare device 110 may be delivered to a target tissue via an insertion device 112. Insertion device 112 may be similar to insertion device 12 and may include any device configured to deliver medical instruments, such as, snare device 110, into a subject's body, and include any appropriate cross-sectional shape. Similar to insertion device 12, insertion device 112 may be inserted into a variety of body openings, lumens, and/or cavities.

Once positioned within the subject's body, a user may move snare device 110 between an extended state (FIG. 2) and a retracted state (not shown). In the extended state, snare device 110 may extend distally out of the distal end of insertion device 112, and snare device 110 may be caused to expand to surround or otherwise engage, grasp, and/or collect tissue. In moving from the extended state to the retracted state, snare device 110 may be drawn into the distal end of insertion device 112, and snare device 110 may be caused to contract to resect tissue.

Snare device 110 may include any appropriate material, such as, for example, Nitinol. Snare device 110 may be heat set into an arcuate, circular, or otherwise curved shape loop including legs 120 as shown in FIG. 2, and may include an atraumatic tip 116. Snare device 110 may further include magnetic material 118 disposed along portions thereof. For example, magnetic material 118 may be positioned along legs 120 of snare device 110, at portions of snare device 110 proximate insertion device 112 when snare device 110 is in the extended state. Additionally, insertion device 112 may include a magnet 122 positioned along a distal portion thereof. For example, magnet 122 may include an annular magnet encircling the distal end of snare device 110. It is understood, however, the disclosure is not so limited. Rather, magnet 122 may include any one or more magnets positioned along the distal end of insertion device 112. For example, one or more magnets 122 of any appropriate shape, construction, and arrangement may be positioned along the distal portion of insertion device 112. For example, one or more discrete or continuous magnets 122 having a rectangular cross-sectional shape may be positioned, coupled, or otherwise disposed adjacent the distal end of insertion device 112. It is understood, however, other cross-sectional shapes are within the scope of this disclosure. Additionally or alternatively, in some examples, magnet 122 may be embedded within insertion device 112. Magnet 122 may be, for example, a super magnet.

Figure 3A:
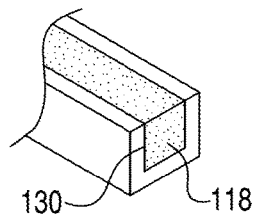
FIGS. 3A and 3B depict exemplary cross-sectional configurations from the snare device of FIG. 2.
Figure 3B:
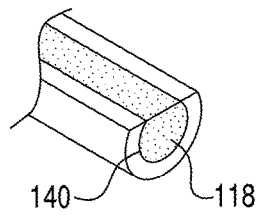

Magnetic material 118 may be disposed within one or more channels of legs 120 of snare device 110. For example, as shown in FIG. 3A, legs 120 may have a rectangular cross-sectional shape including a rectangular channel 130 configured for receipt of magnetic material 118 therein. Alternatively, as shown in FIG. 3B, legs 120 may have a circular cross-sectional shape including a rounded, circular, or partial circular shaped channel 140 configured for receipt of magnetic material 118 therein. In either configuration, magnetic material 118 may be printed, embedded, or otherwise disposed within channel 130 or 140. Channels 130 and/or 140 may be produced in any appropriate fashion, such as, for example, via femto-second laser processing. Magnetic material 118 may include any appropriate material such as, for example, a super magnetic material. By way of example only, magnetic material 118 may be neodymium based.

Magnet 122, and/or magnetic material 118 may be configured as an electromagnet and as such, may be selectively activated and deactivated so as to cooperate with magnetic material 118 or magnet 122, respectively. That is, for example, electricity may be delivered to magnet 122 or magnetic material in any appropriate manner (e.g., a conductive wire) so as to energize magnet 122 or magnetic material to produce a magnetic field. Upon energizing, magnet 122 or magnetic material 118 may be attracted to magnetic material 118 or magnet, respectively. Further, when delivery of electricity to magnet 122 or magnetic material is ceased, the magnetic field will no longer be produced, thus eliminating interaction between magnet 122 and magnetic material 118. Additionally or alternatively, the magnetic field produced by magnet 122 or magnetic material 118 have an adjustable magnitude or strength. For example, a dial may be coupled with the handle so as to allow a user to increase or decrease the magnitude or strength of the magnetic field produced by magnet 122 or magnetic material 118.

For example, magnet 122 may be deactivated during movement of snare device 110 between the extended state (FIG. 2) and the retracted state (not shown). Once deployed, however, magnet 122 may be activated so as to attract magnetic material 118. Due to the interaction of magnet 122 and magnetic material 118, legs 120 of snare device 110 may be maintained in the extended state as shown in FIG. 2. Additionally, due to the attractive force between magnet 122 and magnetic material 118, legs 120 of snare device 110 may be limited or prevented from twisting, folding, and/or rotating about longitudinal axis 114 onto itself. In other words, the interaction between magnet 122 and magnetic material 118 facilitates resecting, grasping, and/or collecting tissue while limiting or preventing snare device 110 from bending and/or deflecting away from a plane of a layer of tissue, which may reduce the snare's ability to ensnare the desired tissue.

In an additional and/or alternative aspect, magnetic material 118 in each leg 120 may have a like magnetic poles and as such, may be repelled by one another. Accordingly, in such an arrangement, repulsive forces between magnetic material 118 in each leg 120 may limit or prevent twisting, folding, and/or rotating about longitudinal axis 114 onto itself. In such an arrangement, magnet 122 may not be required.

Figure 4:
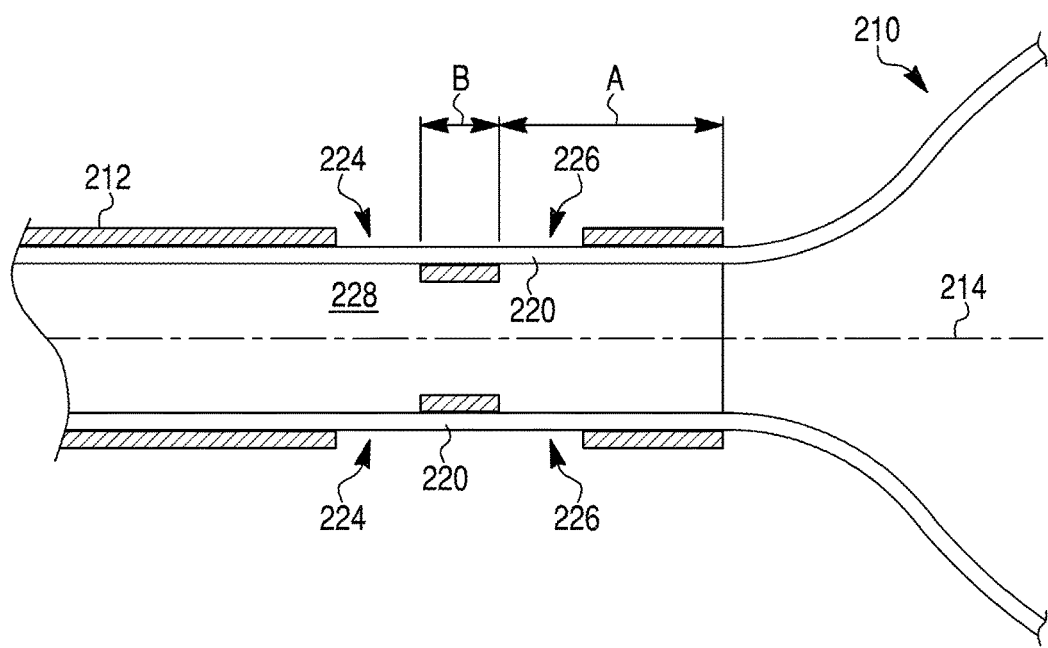
FIG. 4 depicts a cross-sectional view of an exemplary snare device, according to other aspects of the present disclosure.

In another example, as shown in FIG. 4, an insertion device 212 may include openings 224 and 226 through which legs 220 of snare device 210 may be weaved therethrough. Other than openings 224 and 226, insertion device 212 may be similar in construction and purpose as insertion device 12. Accordingly, insertion device 212 may include any device configured to deliver medical instruments, such as snare device 210, into a subject's body. Similar to insertion device 12, insertion device 212 may be inserted into a variety of body openings, lumens, and/or cavities and include any appropriate cross-sectional shape. Once positioned within the subject's body, a user may move snare device 210 between an extended state (FIG. 4) and a retracted state (not shown). In the extended state, snare device 210 may extend distally out of the distal end of insertion device 212, and snare device 210 may be caused to expand to surround or otherwise engage, grasp, and/or collect tissue. In moving from the extended state to the retracted state, snare device 210 may be drawn into the distal end of insertion device 212, and snare device 210 may be caused to contract to resect tissue.

Snare device 210 may include any appropriate material, such as, for example, Nitinol, which may be heat set into an arcuate, circular, or otherwise curved shape loop including legs 220 and an atraumatic tip (not shown). As shown in FIG. 4, each leg 220 may extend distally through a lumen 228 of insertion device 212, extend through first opening 224, return through second opening 226, and extend distally out of the distal end of insertion device 212. Openings 224 and 226 may be formed in any appropriate manner. For example, openings 224 and 226 may be formed by punching, cutting, etc. Subsequently, insertion device 212 may be heated adjacent to openings 224 and 226 such that a portion of insertion device 212 between openings 224 and 226 may be pushed radially inwards towards a longitudinal axis 214. Accordingly, each leg 220 may extend generally straight through lumen 228, first opening 224 and second opening 226, without bending. Such an arrangement may reduce friction imparted to legs 210 during use.

As shown in FIG. 4, insertion device 212 may include a pair of first openings 224 diametrically opposed to one another, and a pair of second openings 226 diametrically opposed to one another. Accordingly each leg 220 may extend through a first opening 224 and a second opening 226. In other examples, however, insertion device 212 may include a single first opening 224 and a single second opening 226. As such, only a single leg 220 of snare device 210 may be woven through openings 224 and 226 of insertion device 212.

In either arrangement, the surface of insertion device 212 defining first opening 224 and second opening 226 through which one or more legs 220 of snare 210 may extend may reduce the number of degrees of freedom of legs 220 of snare 210. That is, by virtue of placement of one or more legs 220 through first opening 224 and second opening 226, leg 220 may be held in close proximity to (e.g., against) the inner diameter surface of insertion device 212. This holding may radially and/or rotationally constrain leg 220. As such, legs 220 of snare device 210 may be limited or prevented from twisting, folding, and/or rotating about longitudinal axis 214 toward and/or onto each other. In other words, openings 224 and 226 may facilitate limiting or preventing snare device 210 from bending and/or deflecting away from a plane of a layer of tissue, which may reduce the snare's ability to ensnare the desired tissue. Additionally, the spacing of openings 224 and 226 relative to each other and/or the distal end of insertion device 212 may impact the angle and/or degree of openings of snare device 210. For example, as shown in FIG. 4, a proximal end of each second opening 226 may be positioned at a distance A from the distal end of insertion device 212, and a distal end of each first opening 224 may be positioned at a distance B from the proximal end of a respective second opening 226. Distances A and B may be selected to achieve a desired angle and/or degree of opening of snare device 210. For example, an increase in distance A may impart a decrease in loop diameter when snare device 210 is in the expanded and extended state; thus reducing the amount of tissue that can be surrounded.

Figure 5:
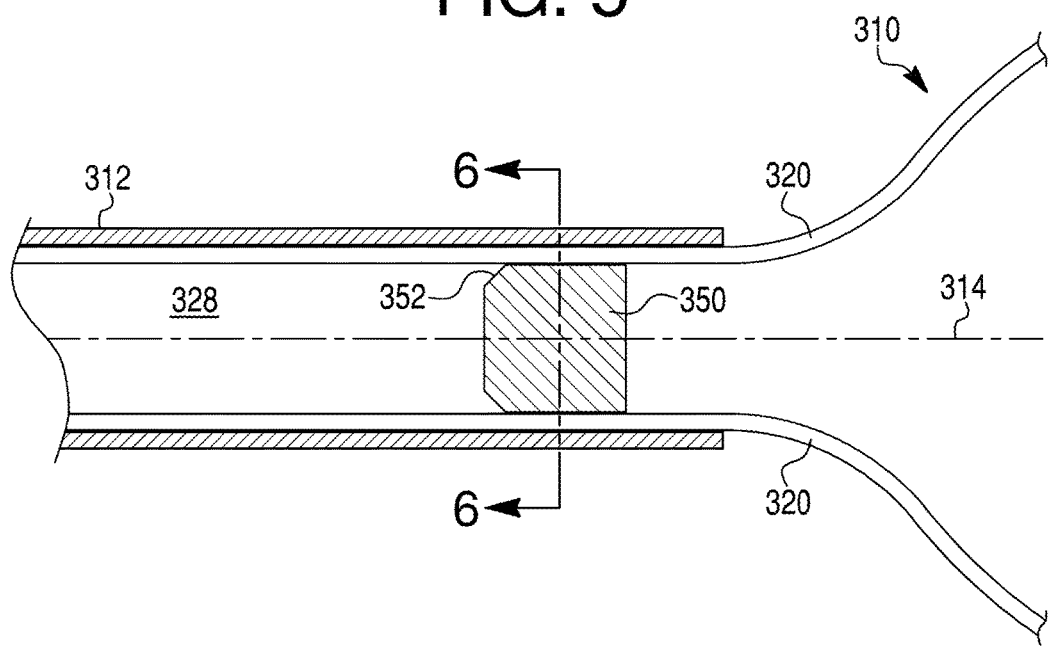
FIG. 5 depicts a cross-sectional view of an exemplary snare device, according to further aspects of the present disclosure.
Figure 6:
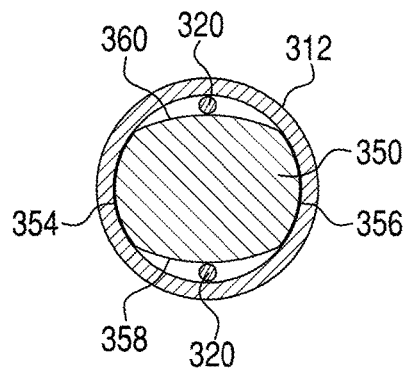
FIG. 6 depicts another cross-sectional view of the exemplary snare device of FIG. 5, taken along line 6-6 of FIG. 5.

In a further example, as shown in FIGS. 5 and 6, a snare device 310 may extend along a longitudinal axis 314. Snare device 310 may be delivered to a target tissue via an insertion device 312 similar to insertion device 12. Accordingly, insertion device 312 may include any device configured to deliver medical instruments, such as, for example, snare device 310, into a subject's body. Similar to insertion device 12, insertion device 312 may be inserted into a variety of body openings, lumens, and/or cavities and include any appropriate cross-sectional shape. Once positioned within the subject's body, a user may move snare device 310 between an extended state (FIG. 5) and a retracted state (not shown). In the extended state, snare device 310 may extend distally out of the distal end of insertion device 312, and snare device 310 may be caused to expand to surround or otherwise engage, grasp, and/or collect tissue. In moving from the extended state to the retracted state, snare device 310 may be drawn into the distal end of insertion device 312, and snare device 310 may be caused to contract to resect tissue.

Snare device 310 may include any appropriate material, such as, for example, Nitinol, which may be heat set into an arcuate, circular, or otherwise curved shape loop including legs 320, and may include an atraumatic tip (not shown).

As shown in FIG. 5, insertion device 312 may further include a space occupier 350 positioned within a lumen 328 of insertion device 312. Space occupier 350 may include, for example, a polymer plug. Alternatively, space occupier 350 may include any appropriate material. Space occupier may be coupled to insertion device 312 in any appropriate fashion, such as, for example, fusing, embedding, and/or the use of adhesives. As shown in FIG. 5, space occupier 350 may include one or more tapered portions 352. For example, a proximal end of space occupier 350 may include an annular tapered portion 352. Tapered portion 352 may be configured to urge legs 320 radially outwardly of longitudinal axis 314 and toward an interior wall of insertion device 312.

Space occupier 350 may limit the space within lumen 328 in which legs 320 may move. This limiting may reduce the number of degrees of freedom of legs 320 of snare 310. As such, legs 320 of snare device 310 may be limited or prevented from twisting, folding, and/or rotating about longitudinal axis 314 onto itself. In other words, space occupier 350 may facilitate limiting or preventing snare device 310 from bending and/or deflecting away from a plane of a layer of tissue, which may reduce the snare device's ability to ensnare the desired tissue. That is, space occupier 350 may maintain the snare 310 in a single plane, and/or may maintain a rotational position of each leg 320.

Space occupier 350 may include any appropriate cross-sectional shape configured to occupy lumen 328 of insertion device 312. For example, as shown in FIG. 6, space occupier 350 may have a rounded rectangular cross-sectional shape. That is, as shown, first side 354 and second side 356 of space occupier may be arcuate, rounded, or otherwise shaped so as to cooperate (e.g., mate with) the interior wall of insertion device 312. Further, third side 358 and fourth side 360 may be arcuate, rounded, or otherwise shaped so as to extend radially outwardly to abut against legs 320 and limit movement of legs 320 relative to insertion device 312 with the assistance of the interior wall of insertion device 312. Third side 358 and fourth side 360 may help guide legs 320 to diametrically opposing portions of the interior of insertion device 312, due to the limitations on movement of legs 320 resulting from the shape of the gaps between third and fourth sides 358 and 360 and the interior wall of insertion device 312, the gaps narrowing at their edges as shown in FIG. 6. It is understood, however, that space occupier is not limited to such a cross-sectional shape. Rather, space occupier 350 may include any cross-sectional shape configured to occupy lumen 328 of insertion device 312. Such cross-sectional shapes may include a circular, square, polygonal, and/or irregular shape.

Figure 8:
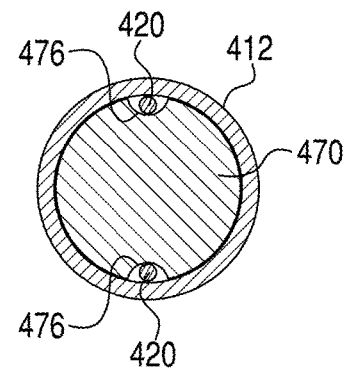
FIG. 8 depicts another cross-sectional view of the exemplary snare device of FIG. 7, taken along line 8-8 of FIG. 7.

For example, in another exemplary aspect, as shown in FIGS. 7 and 8, a space occupier 470 may have an hourglass cross-sectional shape. That is, as shown in FIG. 8, space occupier 470 may define detents, grooves, and/or channels 476 configured to receive legs 420 therethrough. As such, channels 476 may be configured to urge legs 420 radially outwardly of longitudinal axis 414 and toward an interior wall of insertion device 412. As such, space occupier 470 may limit the space within lumen 428 in which legs 420 may move, keeping legs 420 at diametrically opposite regions in the interior of insertion device 412, or otherwise reducing the number of degrees of freedom of legs 420 of snare 410. Accordingly, legs 420 of snare device 410 may be limited or prevented from twisting, folding, and/or rotating about longitudinal axis 414 onto itself. That is, space occupier 470 may maintain the snare 410 in a single plane, and/or may maintain a rotational position of each leg 420.

Additionally, as described above, and as shown in FIG. 7, a proximal end of legs 420 may be coupled to an actuating member such as actuating member 474 via a securement device such as, for example, a hypotube or crimp 472. Actuating member 474 may extend proximally to a handle (not shown) configured to remain outside of the patient's body during a procedure and may allow a user to control the snare device 410, for example, by applying an axially directed pushing or pulling force on one or both of the legs 420. Alternatively, actuating member 474 and securement device 472 may be omitted, and each of legs 420 may extend proximally to the handle to allow a user to control snare device 410, to transition snare device 410 between the extended and retracted states.

Figure 9A:
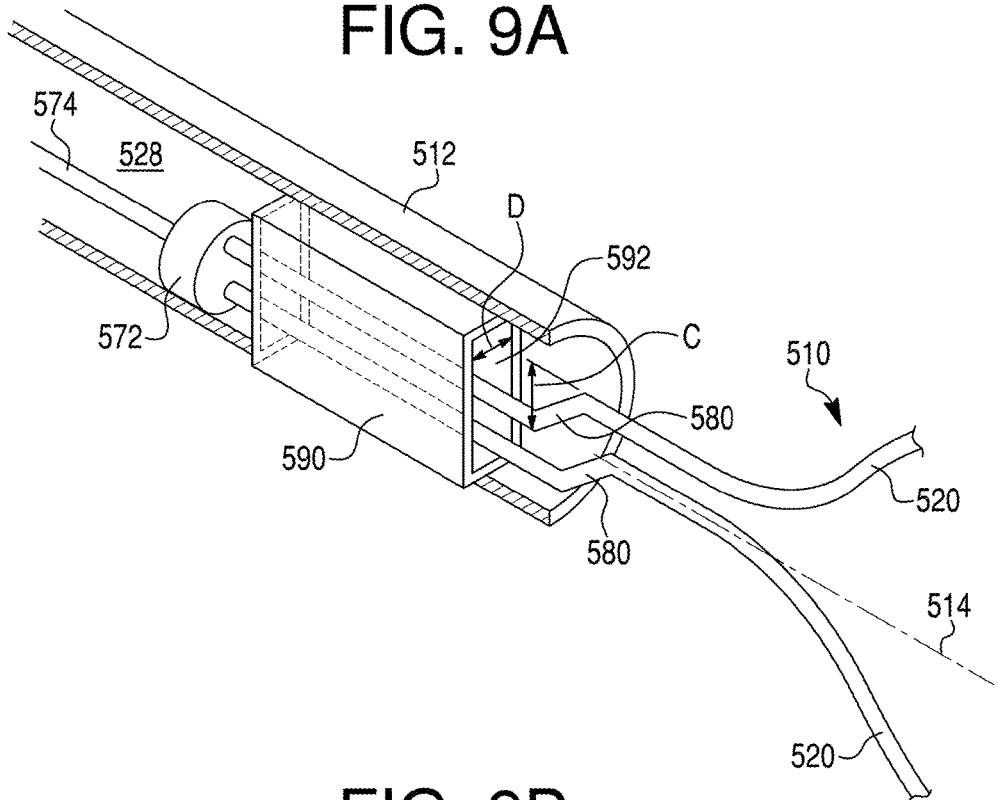
FIG. 9A is a cut-away view depicting an exemplary snare device in an extended state, according to still further aspects of the present disclosure.
Figure 9B:
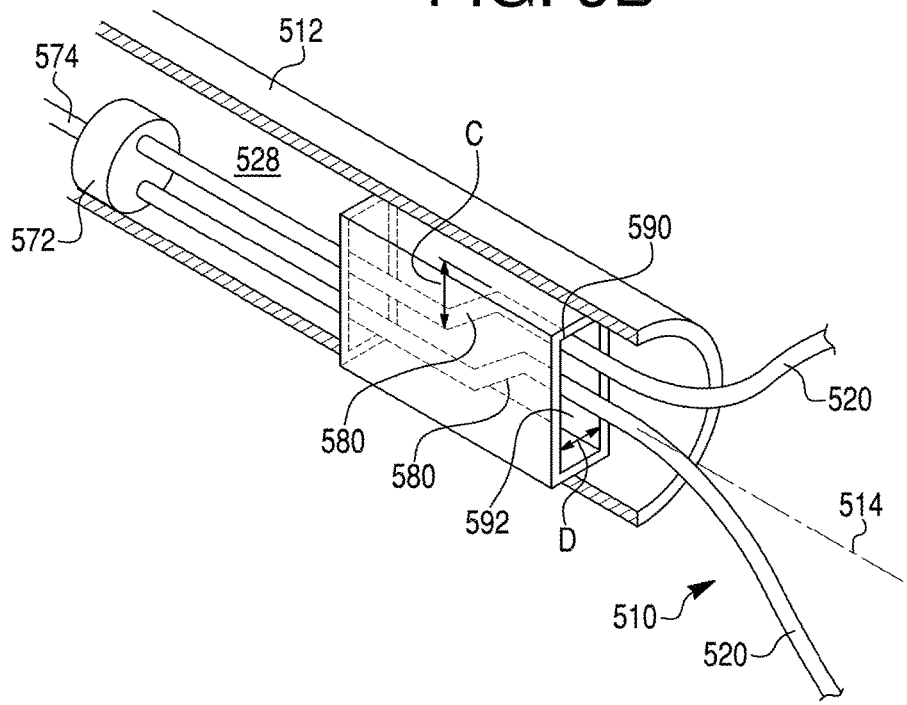
FIG. 9B depicts the exemplary snare device of FIG. 9A, in a partially retracted state.

In another exemplary arrangement, as shown in FIGS. 9A and 9B, a snare device 510 may extend along a longitudinal axis 514. Snare device 510 may be delivered to a target tissue via an insertion device 512. Insertion device 512 may be similar to insertion device 12 and may include any device configured to deliver medical instruments, such as, for example, snare device 510, into a subject's body, and may include any appropriate cross-sectional shape. Similar to insertion device 12, insertion device 512 may be inserted into a variety of body openings, lumens, and/or cavities. Once positioned within the subject's body, a user may move snare device 510 between an extended state (FIG. 9A), a partially retracted state (FIG. 9B), and a fully retracted state (not shown). In the extended state, snare device 510 may extend distally out of the distal end of insertion device 512, and snare device 510 may be caused to expand to surround or otherwise engage, grasp, and/or collect tissue. In moving from the extended state to the partially-retracted state, and then to the retracted state, snare device 510 may be drawn in to the distal end of insertion device 512, and snare device 510 may be caused to contract to resect tissue.

Snare device 510 may include any appropriate material, such as, for example, Nitinol. Snare device 510 may be heat set into an arcuate, circular, or otherwise curved shape loop including legs 520, and may include an atraumatic tip (not shown). Additionally, similar to snare device 410, a proximal end of legs 520 may be coupled to an actuating member, such as actuating member 574, via a securement device, such as a hypotube or crimp 572. Actuating member 574 may extend proximally to a handle (not shown) configured to remain outside of the patient's body during a procedure and may allow a user to control the snare device 510, for example, by applying an axially directed pushing or pulling force on one or both of the legs 520. Alternatively, actuating member 574 and securement device 572 may be omitted, and each of legs 520 may extend proximally to the handle to allow a user to control snare device 510, to transition snare device 510 between the extended and retracted states.

As shown in FIG. 9A, for example, each leg 520 of snare device 510 may include a geometric feature such as a bend, kink, and/or jog 580 configured to engage or otherwise cooperate with an insert 590 received within a lumen 528 of insertion device 512. While jogs 580 are depicted in FIG. 9A, as extending in similar directions, the disclosure is not so limited. Rather, jogs 580 may extend in different and/or opposite directions. Insert 590 may be coupled to insertion device 512 in any appropriate fashion, such as, for example, fusing, embedding, and the use of adhesives. Further, insert 590 may be positioned within lumen 528 at any appropriate axial location along a longitudinal axis 514. That is, placement of insert 590 within lumen 528 may be moved proximally or distally so as to limit or prevent rotation of legs 520 at different stages of extension and retraction of snare device 510 during use. Additionally, the total axial length of insert 590 along longitudinal axis 514 may be minimized so as to minimize stiffness of the distal end of insert device 512. Alternatively, the total axial length of insert 590 along longitudinal axis 514 may be maximized so as to limit or prevent rotation of legs 520 during a plurality of stages of retraction of legs 520 with respect to insert 590.

Insert 512 may include a through passageway 592 configured for passage of legs 520 therethrough. Through passageway 592 may have, for example, a rectangular cross-sectional shape having a width D sized to receive jog 580 of each leg 520 as the snare device 510 transitions between the extended and retracted states. For example, jog 520 may have a span C configured to be received within passageway 592 with minimal clearance, as shown in FIG. 9B. That is, span C may be two times greater than width D. Alternatively, span C may be less than two times greater than width D, or more than two times greater than with D, depending on factors, such as, the desired level of retracting force needed to retract snare device 510. Width D may be, for example, equal to, or slightly greater than, a diameter of legs 520. Such dimensions may increase radial stability of snare device 510. Additionally the angle of segments forming jog 580 can be adjusted to make retraction smooth. For example, reducing the angle may facilitate smoother retraction. As used herein, the terms "about," "substantially," and "approximately," may indicate a range of values within +/−5% of a stated value. Accordingly, jog 580 may be received within insert 590 only if jog 580 is rotated such that span C is angled with respect to width D. For example, during retraction of snare device 510 into insertion device 512, insert 590 may receive jog 580 therein. However, if the span C of jog 580 is oriented in the direction of width D, jog 580 may abut a distal end of insert 590 and may, in such an orientation, been inhibited from entering insert 590. However, due to the interaction of insert 590 with jog 580, jog 580 may be urged so as to rotate, enabling jog 580 to enter insert 590. Once received within insert 590, the interior walls of insert 590 within through passageway 592 may limit the ability of jogs 580 to rotate about one another, thereby limiting or preventing legs 520 of snare device 510 from rotating about one another, thereby reducing the number of degrees of freedom of legs 520. Accordingly, legs 520 of snare device 510 may be limited or prevented from twisting, folding, and/or rotating about longitudinal axis 514 onto itself. That is, insert 590 may maintain the snare device 510 in a single plane, and/or maintain a rotational position of each leg 520.

Figure 10:
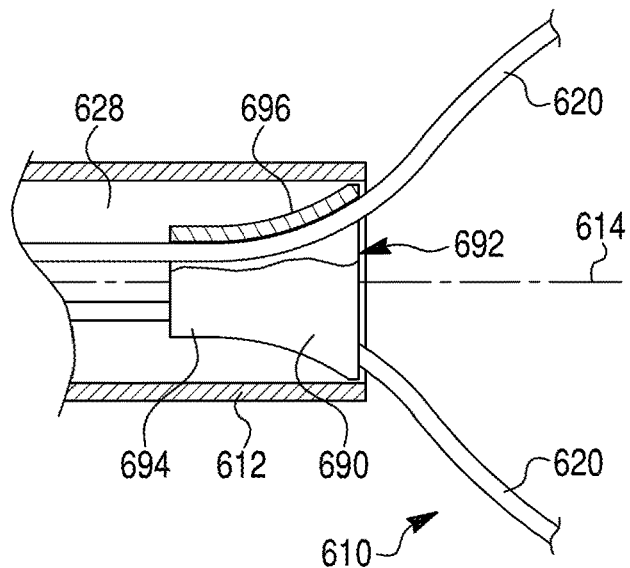
FIG. 10 depicts a cross-sectional view of an exemplary snare device, according to still further aspects of the present disclosure.

In another exemplary arrangement, as shown in FIG. 10, snare device 610 may extend along a longitudinal axis 614. Snare device 610 may be delivered to a target tissue via an insertion device 612. Insertion device 612 may be similar to insertion device 12 and may include any device configured to deliver medical instruments, such as snare device 610, into a subject's body, and may include any appropriate cross-sectional shape. Similar to insertion device 12, insertion device 612 may be inserted into a variety of body openings, lumens, and/or cavities. Once positioned within the subject's body, a user may move snare device 610 between an extended state and a retracted state (not shown). In the extended state, snare device 610 may extend distally out of the distal end of insertion device 612, and snare device 610 may be caused to expand to surround or otherwise engage, grasp, and/or collect tissue. In moving from the extended state to the retracted state, snare device 610 may be drawn in to the distal end of insertion device 612, and snare device 610 may be caused to contract to resect tissue. Snare device 610 may include any appropriate material, such as, for example, Nitinol. Snare device 610 may be heat set into an arcuate, circular, or otherwise curved shape loop including legs 620 shape, and may include an atraumatic tip (not shown).

In the extended state, snare device 510 may extend distally out of the distal end of insertion device 512, and snare device 510 may be caused to expand to surround or otherwise engage, grasp, and/or collect tissue. In moving from the extended state to the partially-retracted state, and then to the retracted state, snare device 510 may be drawn in to the distal end of insertion device 112, and snare device 510 may be caused to contract to resect tissue.

An insert 690 may be received within a lumen 628 of insertion device 612. Insert 690 may be coupled to insertion device 612 in any appropriate fashion, such as, for example, fusing, embedding, and the use of adhesives. Insert 612 may include a through passageway 692 configured for passage of legs 620 therethrough. Through passageway 692 may define a first portion 694 configured to receive legs 620 with minimal clearance, while second portion 696 may have a flared shape configured to receive legs 620 with a greater amount of clearance relative to first portion 694. Accordingly, first portion 694 may be configured to reduce the number of degrees of freedom of legs 620 thereby limiting or preventing legs 620 from twisting, folding, and/or rotating about longitudinal axis 614 onto itself. Meanwhile, second portion 696, via the flared shape, may assist legs 620 in transitioning between the extended and retracted states by guiding legs 620 towards the arcuate, circular, or otherwise curved shape loop. That is, insert 690 may maintain the snare device 610 in a single plane, and/or maintain a rotational position of each leg 620.

Figure 11:
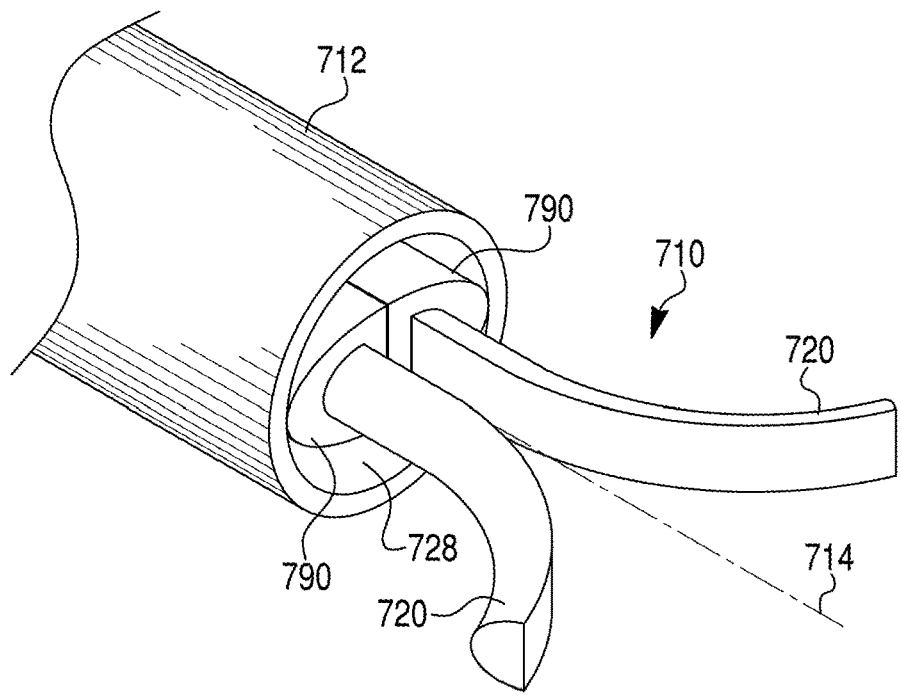
FIG. 11 depicts an exemplary snare device according to still further aspects of the present disclosure.

Alternatively, in another exemplary arrangement, as shown in FIG. 11, a snare device 710 may extend along a longitudinal axis 714. Snare device 710 may be delivered to a target tissue via an insertion device 712. Insertion device 712 may be similar to insertion device 12 and may include any device configured to deliver medical instruments, such as snare device 710, into a subject's body, and may include any appropriate cross-sectional shape. Similar to insertion device 12, insertion device 712 may be inserted into a variety of body openings, lumens, and/or cavities. Once positioned within the subject's body, a user may move snare device 710 between an extended state and a retracted state (not shown). In the extended state, snare device 710 may extend distally out of the distal end of insertion device 712, and snare device 710 may be caused to expand to surround or otherwise engage, grasp, and/or collect tissue. In moving from the extended state to the retracted state, snare device 710 may be drawn in to the distal end of insertion device 712, and snare device 710 may be caused to contract to resect tissue. Snare device 710 may include any appropriate material, such as, for example, Nitinol. Snare device 710 may be heat set into an arcuate, circular, or otherwise curved shape loop including legs 720 shape, and may include an atraumatic tip (not shown).

In the extended state, snare device 610 may extend distally out of the distal end of insertion device 612, and snare device 610 may be caused to expand to surround or otherwise engage, grasp, and/or collect tissue. In moving from the extended state to the retracted state, snare device 610 may be drawn in to the distal end of insertion device 612, and snare device 610 may be caused to contract to resect tissue.

In another exemplary arrangement, a pair of D-shaped inserts 790, in which the flats of the D shape are oriented towards a central longitudinal axis 714 of insertion device 712, may be received within a lumen 728 of insertion device 712. Inserts 790 may be coupled to an interior surface of insertion device 712 in any appropriate fashion, such as, for example, fusing, embedding, and the use of adhesives. Inserts 790 may include channels, guides, or passageways configured to receive legs 720 therethrough. As such, legs 720 may have a cross-sectional shape corresponding to passageways 790. That is, legs 720 may have a D-shaped cross-sectional shape, in which the flats of the D or oriented towards the central longitudinal axis 714 of insertion device 712. Accordingly, legs 720 may be configured to cooperate with passageways 790 so as to transition legs between the extended and retracted states. That is, due to the interaction between legs 720 and passageways 790, legs 720 may be limited or prevented from twisting, folding, and/or rotating about longitudinal axis 714 onto itself. That is, passageways 790 may maintain the snare device 710 in a single plane, and maintain a rotational position of each leg 720. Although not shown, each of passageways 790 may be enlarged so as to each encompass half of lumen 728. In such an arrangement, passageways 790 need not be coupled to an interior surface of insertion device 712. Rather, interaction between passageways 790 may limit or prevent rotational movement of passageways 790 about each other.

While principles of the present disclosure are described herein with reference to illustrative aspects for particular applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the disclosure is not to be considered as limited by the foregoing description.

We claim:

1. A medical device, comprising:
   an insertion device having a proximal end, a distal end, and a lumen extending longitudinally therethrough;
   a snare device configured to transition between a retracted state within the lumen of the insertion device, and an extended state extending distally of the insertion device, the snare device comprising a wire; and
   a space occupier disposed within the lumen of the insertion device and fixedly coupled to the insertion device, wherein the space occupier has an outermost surface completely surrounding a central longitudinal axis of the space occupier, wherein the space occupier is configured to maintain legs of the snare device in an open snare loop configuration in the extended state, wherein in the open snare loop configuration, the wire comprises an arcuate loop, and wherein each of the legs is positioned radially outward of the outermost surface.

2. The medical device of claim 1, wherein the space occupier has a rounded rectangular cross-sectional shape.

3. The medical device of claim 1, wherein the space occupier has an hourglass cross-sectional shape.

4. The medical device of claim 1, wherein the space occupier includes a polymer plug.

5. The medical device of claim 1, wherein the space occupier is solid in a first cross section along the central longitudinal axis and a second cross section perpendicular to the first cross section.

6. The medical device of claim 1, wherein the space occupier has a first pair of sides extending longitudinally, and a second pair of sides extending longitudinally, wherein a first length of each of the first pair of sides measured in a plane perpendicular to the longitudinal axis is greater than a second length of each of the second pair of sides measured in the plane.

7. The medical device of claim 6, wherein each of the second pair of sides mates with a surface defining the lumen.

8. The medical device of claim 6, wherein a first gap is between a first of the first pair of sides and a surface defining the lumen, and wherein a second gap is between a second of the first pair of sides and the surface defining the lumen.

9. The medical device of claim 8, wherein a first of the legs of the snare device passes through the first gap, and wherein a second of the legs of the snare device passes through the second gap.

10. The medical device of claim 1, wherein a proximal end of the space occupier includes a tapered portion extending annularly about the proximal end.

11. A medical device, comprising:
an insertion device having a proximal end, a distal end, and a lumen extending therethrough;
a snare device configured to transition between a retracted state within the lumen of the insertion device, and an extended state extending distally of the insertion device, the snare device comprising a wire; and
a space occupier disposed within the lumen of the insertion device and fixedly coupled to the insertion device, wherein the space occupier has an outermost surface completely surrounding a central longitudinal axis of the space occupier, wherein the space occupier is configured to maintain legs of the snare device in an open snare loop configuration in the extended state, wherein, in the open snare loop configuration, the wire comprises an arcuate loop, and wherein the space occupier is solid in a first cross section along the central longitudinal axis and a second cross section perpendicular to the first cross section.

12. The medical device of claim 11, wherein the space occupier has a rounded rectangular cross-sectional shape.

13. The medical device of claim 11, wherein the space occupier has a first pair of sides extending longitudinally, and a second pair of sides extending longitudinally, wherein a first length of each of the first pair of sides measured in a plane perpendicular to the longitudinal axis is greater than a second length of each of the second pair of sides measured in the plane.

14. The medical device of claim 13, wherein each of the second pair of sides mates with a surface defining the lumen.

15. The medical device of claim 13, wherein a first gap is between a first of the first pair of sides and a surface defining the lumen, and wherein a second gap is between a second of the first pair of sides and the surface defining the lumen.

16. The medical device of claim 15, wherein a first of the legs of the snare device passes through the first gap, and wherein a second of the legs of the snare device passes through the second device.

17. The medical device of claim 11, wherein a proximal end of the space occupier includes a tapered portion extending annularly about the proximal end.

18. A medical device, comprising:
an insertion device having a proximal end, a distal end, a longitudinal axis, and a lumen extending therethrough;
a snare device configured to transition between a retracted state within the lumen of the insertion device, and an extended state extending distally of the insertion device, the snare device comprising a wire; and
a space occupier disposed within the lumen of the insertion device and fixedly coupled to the insertion device, the space occupier configured to maintain legs of the snare device in an open snare loop configuration in the extended state, wherein in the open snare loop configuration, the wire comprises an arcuate loop, wherein the space occupier has a first pair of sides extending longitudinally, and a second pair of sides extending longitudinally, wherein each of the second pair of sides mates with a surface defining the lumen, wherein a first gap is between a first of the first pair of sides and the surface defining the lumen, and a second gap is between a second of the first pair of sides and the surface defining the lumen, wherein a first of the legs of the snare device passes through the first gap, and wherein a second of the legs of the snare device passes through the second gap.

19. The medical device of claim 18, wherein a first length of each of the first pair of sides measured in a plane perpendicular to the longitudinal axis is greater than a second length of each of the second pair of sides measured in the plane.

20. The medical device of claim 18, wherein a proximal end of the space occupier includes a tapered portion extending annularly about the proximal end.

* * * * *